US012723031B2

(12) United States Patent
Lu et al.

(10) Patent No.: US 12,723,031 B2
(45) Date of Patent: Sep. 1, 2026

(54) PREPARATION PROCESS OF 1-N-METHYL-2-NITRO-5-HYDROXYMETHYL IMIDAZOLE

(71) Applicant: ASCENTAWITS PHARMACEUTICALS, LTD., Shenzhen (CN)

(72) Inventors: Zhaoqiang Lu, Shenzhen (CN); Jinwei Fan, Shenzhen (CN); Qunhui Huang, Shenzhen (CN); Yanjun Zhang, Shenzhen (CN); Weisu Chen, Shenzhen (CN)

(73) Assignee: ASCENTAWITS PHARMACEUTICALS, LTD., Shenzhen (CN)

( * ) Notice: Subject to any disclaimer, the term of this patent is extended or adjusted under 35 U.S.C. 154(b) by 480 days.

(21) Appl. No.: 18/209,312

(22) Filed: Jun. 13, 2023

(65) Prior Publication Data

US 2024/0425462 A1 Dec. 26, 2024

(51) Int. Cl.
*C07D 233/91* (2006.01)
*G01N 30/02* (2006.01)

(52) U.S. Cl.
CPC ........... *C07D 233/91* (2013.01); *G01N 30/02* (2013.01)

(58) Field of Classification Search
CPC .................................................... C07D 233/91
See application file for complete search history.

(56) References Cited

U.S. PATENT DOCUMENTS

2010/0137254 A1 6/2010 Matteucci et al.

FOREIGN PATENT DOCUMENTS

WO WO-0064864 A1 * 11/2000 ........... C07C 271/20
WO WO 2007/002931 1/2007

OTHER PUBLICATIONS

Liam J. O'Connor et al, Efficient synthesis of 2-nitroimidazole derivatives and the bioreductive clinical candidate Evofosfamide (TH-302)[J]. Organic Chemistry Frontiers, 2015, vol. 2(9): 1026-1029.

* cited by examiner

*Primary Examiner* — Laura L Stockton
(74) *Attorney, Agent, or Firm* — Ballard Spahr LLP

(57) ABSTRACT

The present invention provides a preparation process of 1-N-methyl-2-nitro-5-hydroxymethylimidazole comprising using N,N'-carbonyldiimidazole and 1-N-methyl-2-amino-imidazole-5-carboxylic acid to react at 45~65° C. for a period of time, and then cooling to 15~25° C. for a period of time until the reaction is complete, and then reacting with a reducing agent to finally obtain 1-N-methyl-2-nitro-5-hydroxymethylimidazole. The present invention uses the relatively safe N,N'-carbonyldiimidazole to replace the highly toxic, strong irritating, strong corrosive, and environmentally demanding isobutyl chloroformate. It has the following advantages: CDI is a solid, non-irritating and non-corrosive, favorable for storage, transportation and environmental protection, low requirements on equipment, and less physical harm to operators; the reaction operation is simple and the post-treatment is simple. The reaction temperature is higher than that of using isobutyl chloroformate, so as to speed up the reaction, save the reaction time and energy consumption. The yield is high, the side reaction is less, and the product is easy to purify: after the reaction is complete, extracting, drying, and concentrating under reduced pressure until it is drained to obtain a high purity product.

11 Claims, 2 Drawing Sheets

| No. | Retention time min | Area mAU*min | Peak height mAU | Relative area % |
|---|---|---|---|---|
| 1 | 4.727 | 126.186 | 2144.722 | 99.94 |
| 2 | 6.697 | 0.038 | 0.500 | 0.03 |
| 3 | 8.050 | 0.021 | 0.332 | 0.02 |
| 4 | 11.053 | 0.023 | 0.377 | 0.02 |

PREPARATION PROCESS OF 1-N-METHYL-2-NITRO-5-HYDROXYMETHYL IMIDAZOLE

FIELD OF THE INVENTION

The present invention relates to the technical field of preparing intermediates for the synthesis of Evofosfamide, in particular to the preparation process of 1-N-methyl-2-nitro-5-hydroxymethylimidazole.

BACKGROUND

TH-302 (Evofosfamide, CAS No.: 918633-87-1) is a 2-nitroimidazole-triggered Hypoxia-Activated Prodrug (HAP) of bromo-isophosphoramide. Under hypoxia conditions, an inactive TH-302 prodrug can release bromo isophosphoramide mustard (Br-IPM) that is highly toxic. TH-302 exhibits broad-spectrum biological activity in vivo and in vitro and specific hypoxia-selective activation activity, and activities of inducing H2AX phosphorylation and DNA cross-linking, thereby leading to cell cycle arrest. Therefore, this compound has been used for developing anticancer drugs by many pharmaceutical companies and scientific research institutes.

Research articles published by Meng F (Meng Fanying) et al. have disclosed that TH-302 has broad-spectrum activity against various tumors, and has excellent hypoxia-selective activity-enhancing effect. Studies have shown that the cytotoxicity in vitro of TH-302 in 32 human cancer cell lines under hypoxia conditions is significantly higher than that under normoxic conditions, suggesting that the compound has selective cytotoxicity in cancer cells under hypoxia conditions. The use of human cells over-expressed by one-electron reductase (POR) confirmed the mechanism of enhanced one-electron reductase-dependent activity of TH-302 under hypoxia conditions, as shown in the following Reaction Scheme 1:

The TH-302 prodrug is reduced by cytochrome P450 oxidoreductase to give free radical anion as an intermediate. Owing to its instability, the free radical anion is then decomposed into the cytotoxin Br-IPM with cytotoxicity, which exerts its efficacy by cross-linking with the DNA chain: mainly inactivating DNA by cross-linking with it via alkylation at the 7-position in the guanine structure on DNA, thereby making it being incapable of normal replication to achieve the effect of inhibiting proliferation of (cancer) cells.

Further in-vivo animal model experiments have showed that TH-302 can effectively reduce hypoxia regions in various tumors (Sun, J. D., Liu, Q., Wang, J., Ahluwalia, D., Ferraro, D., Wang, Y., Duan, J. X., Ammons, W. S., Curd, J. G., Matteucci, M. D., & Hart, C. P. (2012). Selective tumor hypoxia targeting by hypoxia-activated prodrug TH-302 inhibits tumor growth in preclinical models of cancer. Clinical cancer research: an official journal of the American Association for Cancer Research, 18(3), 758-770. https://doi.org/10.1158/1078-0432.CCR-11-1980), and result in increased immunotherapeutic efficacy (Jayaprakash, P., Ai, M., Liu, A., Budhani, P., Bartkowiak, T, Sheng, J., Ager, C., Nicholas, C., Jaiswal, A. R., Sun, Y, Shah, K., Balasubramanyam, S., Li, N., Wang, G., Ning, J., Zal, A., Zal, T., & Curran, M. A. (2018). Targeted hypoxia reduction restores T cell infiltration and sensitizes prostate cancer to immunotherapy. The Journal of clinical investigation, 128(11), 5137-5149. https://doi.org/10.1172/JCI96268).

The above findings have indicated that TH-302 still has the potential to be developed as an anticancer drug, and thus there still remains a need to develop a highly-efficient process for preparing or synthesizing TH-302.

The synthesis method of TH-302 was first disclosed by Duan Jianxin (J-X•Duan) in the patent application documents filed by Threshold Company, namely PCT/US2006/025881, WO2007/002931 (the counterpart Chinese patent application with the Publication No. CN101501054A), and in its Examples 22 to 26, the synthesis routes and preparation method (hereinafter referred to as the "Threshold's Reaction Scheme 1

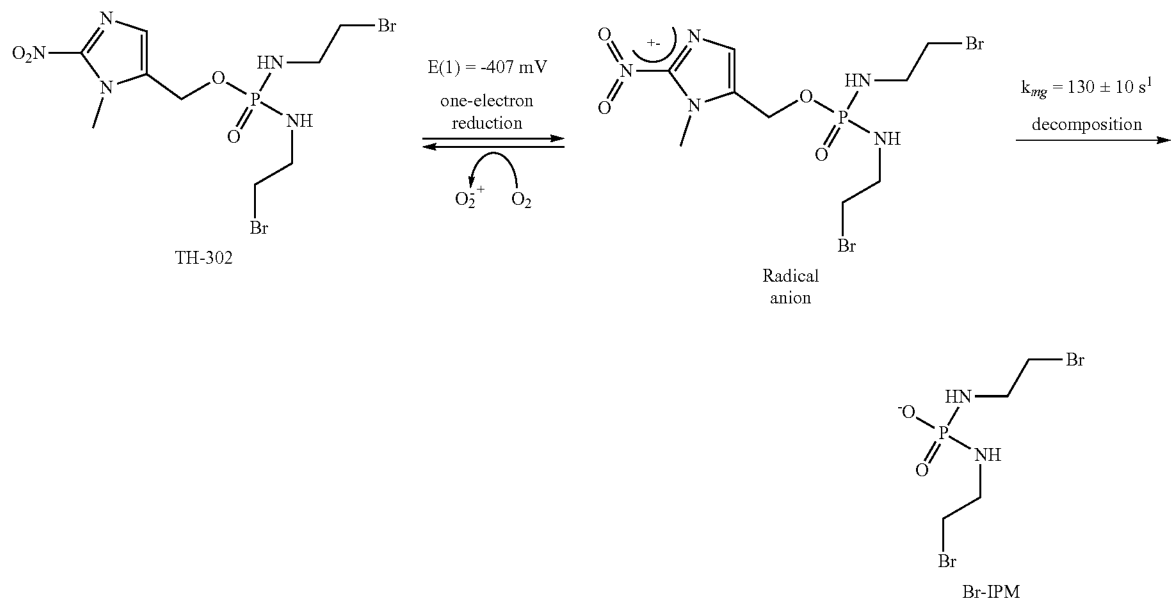

TH-302

Radical anion

Br-IPM method") of the following key intermediate 1-N-methyl-2-nitro-5-hydroxymethyl have been described. The specific routes are shown below:

Synthesis Route 1 of the intermediate in the Threshold's method

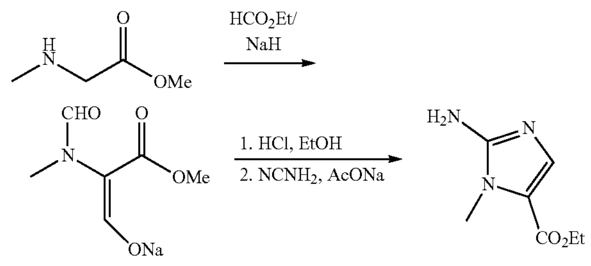

Synthesis Route 2 of the intermediate in the Threshold's method

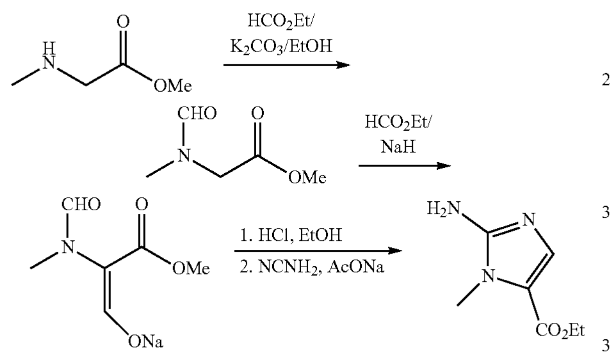

On the basis of ethyl 1-N-methyl-2-aminoimidazole-5-carboxylate, the amino group was converted into nitro group by diazotization reaction:

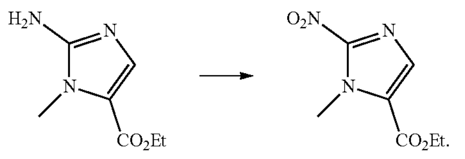

And the acetate was hydrolyzed into carboxylic acid by alkaline hydrolysis:

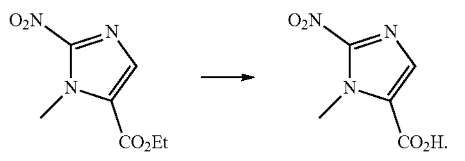

The carboxylic acid was reduced to alcohol hydroxyl group to finally obtain 1-N-methyl-2-nitro-5-hydroxymethylaoimidazole:

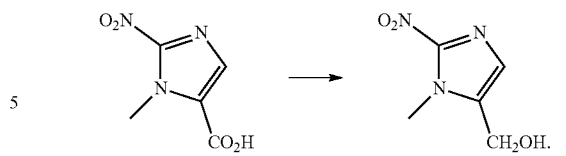

In the above preparation process, the operating procedure of reducing carboxylic acid to alcohol hydroxyl group to finally obtain 1-N-methyl-2-nitro-5-hydroxymethylimidazole is as follows:

The mixture of nitric acid (30.82 g, 180.23 mmol) and triethylamine (140 mL, 285 mmol) in anhydrous THF (360 mL) was stirred, and the reaction mixture was cooled in a dry ice-acetonitrile bath (temperature<−20° C.). Isobutyl chloroformate (37.8 mL, 288 mmol) was added dropwise to the cooled reaction mixture over a period of 10 minutes and stirred for 1 hour, then sodium borohydride (36 g, 947 mmol) was added and water was added dropwise over a period of 1 hour, while maintaining the temperature at or below about 0° C. The reaction mixture was heated to 0° C. The solid was filtered off and washed with THF. The combined THF fraction was evaporated to obtain 1-N-methyl-2-nitro-5-hydroxymethylimidazole as an orange solid (25 g), which was recrystallized from ethyl acetate.

Isobutyl chloroformate used in this method is liquid at room temperature, which has strong irritation and corrosivity, and is unfavorable for storage and transportation in large-scale industrial production. More seriously, the compound is a highly toxic chemical reagent. In the actual operating procedure, it has high requirements for equipment and is very harmful to the operator's body. These factors restrict the use of isobutyl chloroformate as a reaction reagent in industrial production. Therefore, it is necessary to screen other mild, non-toxic or low-toxic reagents to replace isobutyl chloroformate.

SUMMARY OF THE INVENTION

The present invention aims at providing a new preparation process of 1-N-methyl-2-nitro-5-hydroxymethylimidazole.

The present invention specifically adopts the following technical solutions:

One aspect of the present invention provides the following preparation process of 1-N-methyl-2-nitro-5-hydroxymethylimidazole A7:

The process comprises that N,N'-carbonyldiimidazole and 1-N-methyl-2-nitro-5-carboxylic acid imidazole A6 are used to react at 45~65° C. for a period of time, and then cooled to 15~25° C. and reacted for a period of time until the reaction is complete, and then reacted with the reducing agent sodium borohydride or potassium borohydride to finally obtain 1-N-methyl-2-nitro-5-hydroxymethylimidazole A7.

The reaction formula of the preparation process of the present invention is as follows:

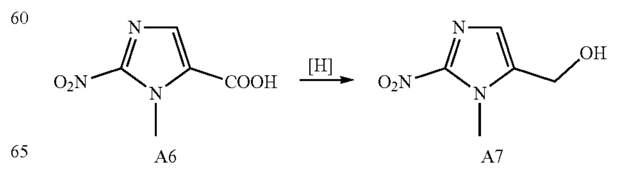

A6 A7

It should be noted that after comparative study, the present invention uses a different activator to activate and then react with the reducing agent sodium borohydride or potassium borohydride. Finally, it is screened and optimized that N,N'-carbonyldiimidazole (CDI) and 1-N-methyl-2-amino-imidazole-5-carboxylic acid A6 react at 45~65° C. for a period of time, and then cool to 15~25° C. and react for a period of time until the reaction is complete, and then react with the reducing agent sodium borohydride or potassium borohydride. In this way, the activation of carboxylic acid can be completed without the use of isobutyl chloroformate which is highly toxic and irritating, and the reaction speed is fast. The whole reaction process is no more than 2 hours, with fewer by-products, which is suitable for industrial large-scale production and use.

In one embodiment of the present invention, the preparation process of 1-N-methyl-2-nitro-5-hydroxymethylimidazole A7 comprises the following steps:

Step 1, N,N'-carbonyldiimidazole is added to a solution of 1-N-methyl-2-nitro-5-carboxylic acid imidazole A6, and the mixture is heated to 45~65° C. and reacts for a period of time, and then is cooled to 15~25° C. and reacts for a period of time until the reaction is complete to obtain liquid A;

Step 2, at 0~5° C., an aqueous solution of sodium borohydride or potassium borohydride is slowly added dropwise to the above liquid A at an appropriate speed so that the temperature of the reaction solution does not exceed 5° C. After dropping, the reaction solution is heated to 15~25° C. until the reaction is complete. An acid is added to adjust the pH value to neutral or weakly acidic, and the organic solvent is removed by concentration under reduced pressure at 40~45°. The residue is extracted with an extractant, and the organic phase is collected. The organic phase is dewatered with a drying agent, and then filtered; the filtrate is collected and concentrated under reduced temperature at 40-45° C. until it is drained to obtain the product A7.

In the improved embodiment, the key is to activate the reaction at two different temperatures, so the two reaction temperatures of 45~65° C. and 15~25° C. in step 1 are the key to reaction control.

In the step 2, when adding the aqueous solution of sodium borohydride or potassium borohydride, it will be exothermic. The temperature should be controlled below 5° C. Of course, too low temperature will prolong the reaction time. Considering the refrigeration conditions in the supply production, the use of ice-salt bath or other refrigerants is safe and environmentally friendly. Controlling the temperature at 0~5° C. can not only make the reaction complete, but also speed up the reaction, which is suitable for industrial production.

After adding sodium borohydride or potassium borohydride, the temperature should be increased to speed up the reaction. The recommended reaction temperature is 15~25° C. In this range of temperature, reaction time is more suitable, and the reaction is more sufficient and complete.

After the reaction is complete, acid is added to neutralize the unreacted sodium borohydride or potassium borohydride to neutral or weakly acidic.

After the reaction is complete and the reaction solution is neutralized by the added acid, the reaction solution is concentrated under reduced pressure at 40-45° C. to remove the organic solvent, that is, concentrated under reduced pressure until it is drained, and the residue is extracted with an extractant.

Since the product A7 has a nitroimidazole alcohol structure and is in aqueous solution, the recommended extractants should be ethyl acetate, methyl acetate, dichloromethane, etc.

The solvent used in the 1-N-methyl-2-nitro-5-carboxylic acid imidazole solution in step 1 is tetrahydrofuran or dioxane, and 1 g of 1-N-methyl-2-nitro-5-carboxylic acid imidazole A6 solute corresponds to 10-30 ml solvent.

It should be noted that in the present invention, step 1 uses a solvent to dissolve 1-N-methyl-2-nitro-5-carboxylic acid imidazole into a solution, mainly to facilitate the reaction with the activator N,N'-carbonyldiimidazole. The solvent used should be a solvent that does not contain a carbon-oxygen double bond group, and can dissolve 1-N-methyl-2-nitro-5-carboxylic acid imidazole. Solvents that can be selected include tetrahydrofuran or dioxane or other ether solvents, and dichloromethane.

The organic phase is dewatered by adding a drying agent, and the selected drying agent is an inorganic salt that can form hydrates, such as anhydrous sodium sulfate, anhydrous calcium sulfate, anhydrous calcium chloride or anhydrous magnesium sulfate.

Preferably, in step 1, the feeding mass ratio of 1-N-methyl-2-nitro-5-carboxylic acid imidazole A6 to N,N'-carbonyldiimidazole is 1:1.10-1.30.

Preferably, in step 1, the reaction time is 20-40 minutes at 45~65° C., and the reaction time is 20-40 minutes at 15~25° C. For example, more preferably, the reaction time is 20-40 minutes at 45~50° C. and 20-40 minutes at 20-25° C.

Preferably, in step 2, the ratio of the amount of the added sodium borohydride or potassium borohydride to the amount of 1-N-methyl-2-nitro-5-carboxylic acid imidazole A6 is 3.0-4.0:1, preferably 3.5-4.0:1.

Preferably, in step 2, the content of sodium borohydride or potassium borohydride in the aqueous solution of sodium borohydride or potassium borohydride is 0.05-0.50 g/ml, preferably 0.05-0.15 g/ml.

Preferably, in step 2, the acid for adjusting the pH value to neutral or weakly acidic is selected from at least one of formic acid, acetic acid and hydrochloric acid.

It should be noted that the essence of adding an acid to adjust the pH value is to add acid to neutralize excess sodium borohydride or potassium borohydride. Therefore, in theory, as long as the pH value is adjusted to neutral, the excess sodium borohydride or potassium borohydride can be completely neutralized. However, in fact, in order to ensure that sodium borohydride or potassium borohydride can be completely neutralized, more acid than the theoretical amount needs to be added; therefore, it is more effective to adjust the pH to weakly acidic, for example by adjusting the pH to 5-6.

It should also be noted that in the procedure of adding acid to neutralize excess sodium borohydride or potassium borohydride in step 2, generally more acid is added, that is, the pH value is adjusted to weakly acidic; in order to more conveniently remove the excess acid later, it is preferred to use an acid with certain volatility, such as formic acid, acetic acid, hydrochloric acid, etc., which can be removed by volatilizing under certain conditions such as vacuum decompression and heating. In one embodiment of the present application, acetic acid is preferred.

Preferably, in step 2, adjust the pH to 5-6.

Preferably, in step 2, the extractant is selected from at least one of ethyl acetate, methyl acetate and dichloromethane. More preferably, the extractant is ethyl acetate.

In one embodiment of the present invention, the preparation process of the present invention further comprises step 3, which refines and purifies the product 1-N-methyl-2-nitro-5-hydroxymethylimidazole obtained by concentration under reduced pressure at 40~45° C. until it is drained; wherein, the refining and purifying include that the product concentrated under reduced pressure is dispersed into ethanol, and filtered, and the filter cake is washed with ethyl acetate to obtain purified 1-N-methyl-2-nitro-5-hydroxymethylimidazole.

It should be noted that step 3 of the present invention is mainly aimed at large-scale production, such as kilogram-level production, which requires further refining and purifying of the product. It is understood that in the large-scale production at the kilogram-level, due to incomplete reaction or other reasons, it is easy to lead to the low purity of the product concentrated under reduced pressure at 40-45° C. Therefore, further refining and purifying is needed. However, for small-scale production, such as the production at hectogram-level and below, the product concentrated under reduced pressure at 40-45° C. can reach a purity of more than 99%; therefore, there is no need for further refining and purifying. Of course, if there is a special requirement for purity, refining and purifying may also be carried out for the production at hectogram-level and below, which is not specifically limited here.

Another aspect of the present invention also provides an HPLC purity detection method for 1-N-methyl-2-nitro-5-hydroxymethylimidazole A7, including the use of a reversed-phase C18 column as a separation chromatographic column; the detection wavelength is 320 nm, the mobile phase A is 0.1% phosphoric acid solution, and the mobile phase B is acetonitrile; the gradient elution program includes the mobile phase A from 95% volume ratio to 10% volume ratio, followed by isocratic elution at 10% volume ratio for a period of time;

1-N-methyl-2-nitro-5-hydroxymethylimidazole A7 peaks in the range of 75%-90% volume ratio of mobile phase A; and the percentage purity of 1-N-methyl-2-nitro-5-hydroxymethylimidazole A7 is calculated by area normalization method based on the peak area of 1-N-methyl-2-nitro-5-hydroxymethylimidazole A7.

Preferably, the chromatographic column is a ZORBAX Eclipse Plus C18 column with a specification of 150*4.6 mm, and the flow rate of the mobile phase is 1.0 ml/min.

The elution procedure is as follows:

| Time/minute | Volume percentage of mobile phase A | Volume percentage of mobile phase B |
|---|---|---|
| 0 | 95 | 5 |
| 30 | 10 | 90 |
| 35 | 10 | 90 |
| 35.1 | 95 | 5 |
| 40 | 95 | 5 |

and

1-N-methyl-2-nitro-5-hydroxymethylimidazole A7 peaks within 3-6 minutes.

The present invention brings about the following beneficial effects:

The present invention proposes the preparation of TH-302 key intermediate 1-N-methyl-2-nitro-5-hydroxymethylimidazole using relatively safe reagent N,N'-carbonyldiimidazole in industrial large-scale production occasions. The main improvement is to use relatively safe N,N'-carbonyldiimidazole instead of highly toxic, strong irritating, strong corrosive, and environmentally demanding isobutyl chloroformate.

The preparation process of the present invention replaces isobutyl chloroformate with N,N'-carbonyldiimidazole (CDI), having the following advantages:

CDI is a solid, non-irritating and non-corrosive, favorable for storage, transportation and environmental protection; it does not have high requirement to equipment and is not harmful to the operator's body;

The reaction operation is simple and the post-treatment is simple; the reaction temperature is higher than that of isobutyl chloroformate, which speeds up the reaction, saves the reaction time and saves the energy consumption; and The yield is high, the side reaction is less, and the product is easy to purify; after the reaction is complete, the product with high purity can be obtained by extracting, drying, and concentrating under reduced pressure until it is drained.

DETAILED DESCRIPTION OF THE INVENTION

Figure 1:
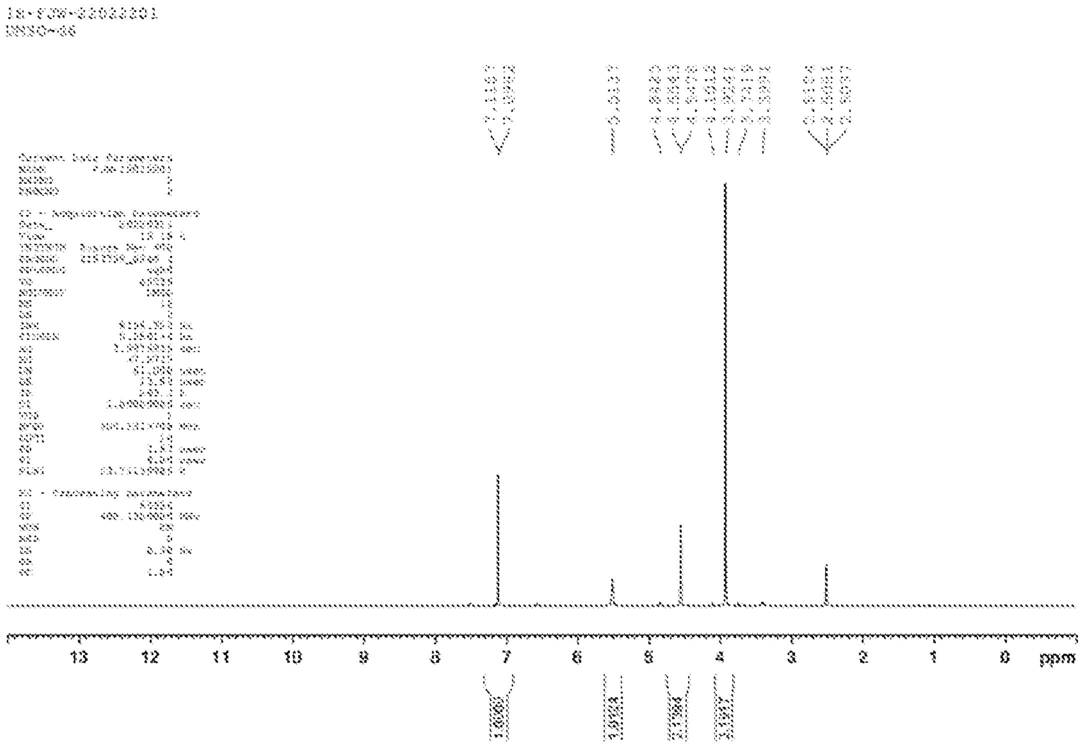
FIG. 1 is the hydrogen spectrum of 1-N-methyl-2-nitro-5-hydroxymethylimidazole A7 prepared in Example 1 of the present invention.

The present invention will be further described in detail below in conjunction with specific examples. The following examples are only for the purpose of further illustrating the present application and should not be understood as restrictions on the present application.

Example 1

The reaction formula for the preparation of 1-N-methyl-2-nitro-5-hydroxymethylimidazole in this example is as follows:

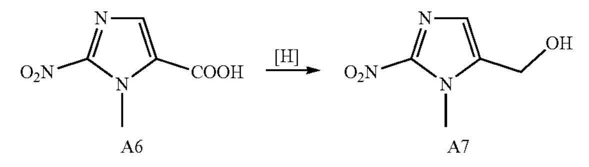

In this example, in the preparation process of 1-N-methyl-2-nitro-5-hydroxymethylimidazole, the specific operating procedure is as follows:

Under the protection of nitrogen gas, 1.4 g of 1-N-methyl-2-nitro-5-carboxylic acid imidazole A6 and 40 ml of anhydrous tetrahydrofuran were added to a 100 ml three-necked flask. The solution was stirred to dissolve, and 1.73 g of N,N'-carbonyldiimidazole (0.010 mol) was added. The reaction was heated to 45~50° C. and reacted for 20 min, and then was cooled to 20-25° C. and reacted for 20 min until the sample as detected by HPLC contained less than 1.0% of the raw material A6. Liquid A was obtained and reserved.

At 0~5° C., 1.24 g sodium borohydride (0.032 mol) and 20 ml $H_2O$ were added to another 100 ml three-necked flask, and stirred to dissolve. The temperature was controlled at 0~5° C. The above liquid A was slowly added dropwise at an appropriate speed so that the temperature of the reaction solution did not exceed 5° C. After dropping, the reaction was heated to 20-25° C. and reacted for 30 min, and then 5 ml of glacial acetic acid was added dropwise. After the addition, the mixture was concentrated under reduced pressure at 40-45° C. until it was drained. The residue was extracted twice with ethyl acetate, 250 ml each time. The extract liquor was combined, and 20.0 g of anhydrous sodium sulfate was added to dry and dewater for 3 h, and filtered; the filtrate was collected and concentrated under reduced pressure at 40~45° C. until it was drained to obtain the product A7.

The product A7 was weighed, and the results showed that the weight of the product A7 prepared in this example was 0.7 g. The ratio of the weight of the actually weighed product A7 to the weight of the A7 that A6 can theoretically generate is used as the yield of this example. The results showed that the yield of the product A7 prepared in this example was 54.26%.

Figure 2:
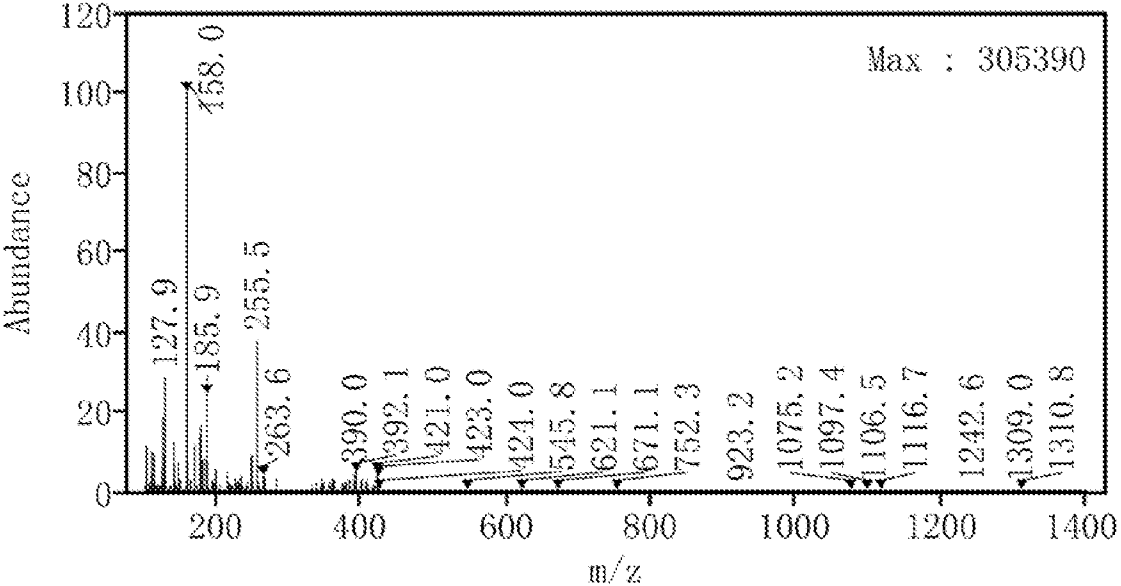
FIG. 2 is the mass spectrum of 1-N-methyl-2-nitro-5-hydroxymethylimidazole A7 prepared in Example 1 of the present invention.

The hydrogen spectrum and mass spectrum of the reaction product prepared in this example were measured, as shown in FIG. 1 and FIG. 2 respectively. The spectrum data is $^1H$-NMR (DMSO-$d_6$, δ/ppm): 3.7419 (3H, s, —$CH_3$), 4.5478 (2H, d, —$CH_2$), 5.5137 (1H, br, —OH), 7.1157 (1H, s, —CH); MS (m/z): 158.0 ($M+H^+$). The results showed that the product A7 prepared in this example was 1-N-methyl-2-nitro-5-hydroxymethylimidazole.

The purity of 1-N-methyl-2-nitro-5-hydroxymethylimidazole A7 product prepared in this example was detected by HPLC. Specifically, the product A7 was dissolved in 50% acetonitrile and then injected into the HPLC instrument for detection. A reversed-phase C18 column was used as the separation chromatographic column, and the detection wavelength was 320 nm. The mobile phase A was 0.1% phosphoric acid solution, and the mobile phase B was acetonitrile. The gradient elution program included the mobile phase A from 95% volume ratio to 10% volume ratio, followed by isocraticelution at 10% volume ratio for a period of time. 1-N-methyl-2-nitro-5-hydroxymethylimidazole A7 peaked in the range of 75%-90% volume ratio of the mobile phase A. The percentage purity of 1-N-methyl-2-nitro-5-hydroxymethylimidazole A7 was calculated by area normalization method based on the peak area of 1-N-methyl-2-nitro-5-hydroxymethylimidazole A7.

Take a commercially available ZORBAX Eclipse Plus C18 column (specification of 150*4.6 mm, 150 mm in length, 4.6 mm in inner diameter) with 3.5 μm particle size filler as an example. The flow rate of the mobile phase was 1.0 ml/min, and the elution procedure was as follows:

| Time/minute | Volume percentage of mobile phase A | Volume percentage of mobile phase B |
|---|---|---|
| 0 | 95 | 5 |
| 30 | 10 | 90 |
| 35 | 10 | 90 |
| 35.1 | 95 | 5 |
| 40 | 95 | 5 |

The results showed that the purity of 1-N-methyl-2-nitro-5-hydroxymethylimidazole A7 prepared in this example was 99.80%.

Example 2

The preparation process of this example was the same as that of Example 1. The difference is that 2.0 g of A6 was fed, and correspondingly 2.47 g of N,N'-carbonyldiimidazole and 1.78 g of sodium borohydride were used. The other steps and conditions were the same as those of Example 1.

Weighing, purity detection and yield calculation were carried out using the same methods as those in Example 1.

The results showed that a total of 1.02 g of A7 was obtained, with a purity of 99.82% and a yield of 55.40%.

Example 3

This example is an exploratory experiment. On the basis of Example 1, isobutyl chloroformate, N,N'-carbonyldiimidazole (CDI), N,N'-dicyclohexylcarbodiimide (DCC), 1-(3-dimethylaminopropyl)-3-ethylcarbodiimide (EDC), trifluoro-s-triazine (2,4,6-trifluoro-1,3,5-triazine) were used as activators respectively, and different reaction time and reaction temperature were tested to explore the effects of different activators, reaction time and reaction temperature on the final A6-A7 conversion process, and the feeding amount of A6 and activator was fixed. The purity and yield of the final A7 were investigated. The specific experimental design is shown in Table 1.

In all reaction groups, the feeding amount of A6 was fixed as 1.40 g.

TABLE 1

Experimental design and result statistics of different experimental groups

| Reaction group | Activator and feeding molar amount | Activation reaction temperature | Reaction time | Reducing reagent | Reduction reaction temperature and time | A7 Purity and Yield |
|---|---|---|---|---|---|---|
| 01 | Isobutyl chloroformate, 0.01 mol | 0-5° C., Ice-salt bath | 15 min, React completely | Sodium borohydride aqueous solution, 0.032 mol | Add dropwise at 0~5° C., React at 20~25° C. for 30 min | 83.35% purity, 51.29% yield |
| 02 | Isobutyl chloroformate, 0.01 mol | Minus 15-Minus 20° C., ethanol cycle | 50 min, React completely | Sodium borohydride aqueous solution, 0.032 mol | Add dropwise at 0~5° C., React at 20~25° C. for 10 min | 94.56% purity, 78.70% yield |
| 03 | CDI, 0.01 mol | 0-5° C., Ice-salt bath; heat to reflux | No reaction for 3 hours; 15 min after reflux | Sodium borohydride aqueous solution, 0.032 mol | Add dropwise at 0~5° C., React at 20~25° C. for 10 min | 10.54% purity, no post-treatment |
| 04 | CDI, 0.01 mol | 60-65° C. reflux | 15 min, React completely | Sodium borohydride aqueous solution, 0.032 mol | Add dropwise at 0~5° C., React at 20~25° C. for 10 min | 20.34% purity, no post-treatment |

TABLE 1-continued

| Experimental design and result statistics of different experimental groups | | | | | | |
|---|---|---|---|---|---|---|
| Reaction group | Activator and feeding molar amount | Activation reaction temperature | Reaction time | Reducing reagent | Reduction reaction temperature and time | A7 Purity and Yield |
| 05 | CDI, 0.01 mol | 45-50° C. | 45 min, React completely | Sodium borohydride aqueous solution, 0.032 mol | Add dropwise at 0~5° C., React at 20~25° C. for 10 min | 68.07% purity, 50.34% yield |
| 06 | CDI, 0.01 mol | React at 45-50° C. for a period of time, then cool to room temperature until the reaction is complete | | Sodium borohydride aqueous solution, 0.032 mol | Add dropwise at 0~5° C., React at 20~25° C. for 10 min | 93.97% purity, 56.75% yield |
| 07 | CDI, 0.01 mol | React at 45~50° C. for 20-40 min, react at 20~25° C. for 20-40 min | | Sodium borohydride aqueous solution, 0.032 mol | Add dropwise at 0~5° C., React at 20~25° C. for 10 min | 98.54% purity, 57.34% yield |
| 08 | DCC, 0.01 mol | 0-5° C., Ice-salt bath; heat to 45° C. | No reaction for 3 hours; 30 min after reflux | Sodium borohydride aqueous solution, 0.032 mol | Add dropwise at 0~5° C., React at 20~25° C. for 10 min | 37.56% purity, 75.23% yield |
| 09 | EDC, 0.01 mol | 0-5° C., Ice-salt bath; heat to 45° C. | No reaction for 3 hours; 60 min after reflux | Sodium borohydride aqueous solution, 0.032 mol | Add dropwise at 0~5° C., React at 20~25° C. for 10 min | 19.86% purity, 56.45% yield |
| 10 | trifluoro-s-triazine, 0.01 mol | 0-5° C., Ice-salt bath; heat to 45° C. | No reaction for 3 hours; 60 min after reflux | Sodium borohydride aqueous solution, 0.032 mol | Add dropwise at 0~5° C., React at 20~25° C. for 10 min | 20.56% purity, 65.84% yield |

Note:
The room temperature in the laboratory is 24° C.

The purity detection and yield calculation were carried out using the same methods as those in Example 1, and the results were shown in Table 1.

The results of Table 1 showed that isobutyl chloroformate is a good activator, and the reaction is fast; the purity and yield are ideal after simple post-treatment, but the isobutyl chloroformate reagent itself is more toxic and irritating.

The activation effect of CDI is closely related to the reaction temperature. If the temperature is too low, the activation cannot be completed; if the temperature is too high, large by-products will be produced after activation and reduction, so the temperature control is the key. After many experiments, it is concluded that high product purity and yield can be obtained by first reacting at 45~65° C. above room temperature for a period of time, such as reacting for 20-40 minutes, and then reacting at 15~25° C. for a period of time, such as reacting for 20-40 minutes. Moreover, it is suggested that the whole reaction time should be controlled within 1 hour or less.

It should be noted that, in theory, DCC, EDC, CDI and trifluoro-s-triazine all can activate A6 to A7. However, the experimental results showed that the reactions using DCC, EDC and trifluoro-s-triazine etc. are not ideal, which means that the activation reaction performance of these reagents is not as good as that of CDI in terms of reaction temperature, reaction time and by-products.

Through experimental comparison, it can be seen that N,N'-carbonyldiimidazole reacts with 1-N-methyl-2-amino-imidazole-5-carboxylic acid A6 at 45~65° C. for 20-40 minutes, and then cools to 15~25° C. and react for 20-40 minutes until the reaction is complete, and then reacts with the reducing agent sodium borohydride or potassium borohydride this A6-A7 conversion process is more suitable for the process preparation conditions of industrial large-scale production.

Example 4

This example is a large-scale amplification example, and the scale of amplification is decagram-, hectogram- to kilogram-level, respectively.

Decagram-Level

Under the protection of nitrogen gas, 17 g of A6 and 490 ml of anhydrous tetrahydrofuran were added to a 2000 ml three-necked flask, and were stirred to dissolve. 21.02 g of N,N'-carbonyldiimidazole (0.13 mol) was added, and heated to 45~50° C. and reacted for 40 min, and then cooled to 20-25° C. and reacted for 40 min, and the sample as detected by HPLC contained less than 1.0% of the raw material A6. Liquid A was obtained and reserved.

At 0~5° C., 15.07 g of sodium borohydride (0.398 mol) and 240 ml of $H_2O$ were added to another 2000 ml three-necked flask, and were stirred to dissolve. The temperature was controlled at 0~5° C. The above liquid A was slowly added dropwise at an appropriate speed so that the temperature of the reaction solution did not exceed 5° C. After dropping, the reaction was heated to 20~25° C. and reacted for 30 min, and then 5 ml of glacial acetic acid was added dropwise. After the addition, the mixture was concentrated under reduced pressure at 40-45° C. until it was drained. The residue was extracted 5 times with ethyl acetate, 600 ml each time. The extract liquor was combined, and anhydrous sodium sulfate was added to dry and dewater for 2 h, and then filtered; the filtrate was collected and concentrated under reduced pressure at 40-45° C. until it was drained to obtain the product A7.

Weighing, purity detection and yield calculation were carried out using the same methods as those in Example 1.

The results showed that 10.3 g of the product was obtained in the decagram-level preparation process, with a purity of 99.94% and a yield of 66.03%.

The HPLC spectrum of 1-N-methyl-2-nitro-5-hydroxymethylimidazole A7 prepared in this example is shown in FIG.

Figure 3:
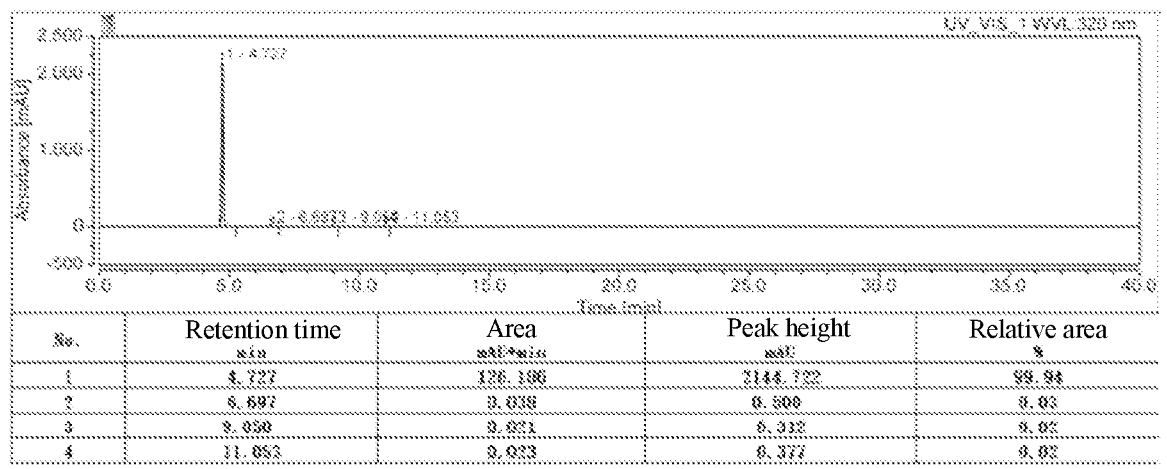
FIG. 3 is the HPLC spectrum of 1-N-methyl-2-nitro-5-hydroxymethylimidazole A7 prepared in the decagram-level experiment of Example 4 of the present invention.

3. The results of FIG. 3 show that 1-N-methyl-2-nitro-5-hydroxymethylimidazole A7 peaked at 4.7 minutes. After several actual tests, it was found that due to the influence of temperature and instrument conditions, the peak time of the product A7 ranged from 3 to 6 minutes, which were normal.

Hectogram-Level

Under the protection of nitrogen gas, 120 g of A6 and 2000 ml of anhydrous tetrahydrofuran were added to a 5000 ml three-necked flask, and were stirred to dissolve. 148.0 g of N,N'-carbonyldiimidazole was added, and heated to 45~50° C. and reacted for 30 min, and then cooled to 20~25° C. and reacted for 30 min, and the sample as detected by HPLC contained less than 1.0% of the raw material A6. Liquid A was obtained and reserved.

At 0~5° C., 106.1 g of sodium borohydride and 2000 ml of $H_2O$ were added to another 5000 ml three-necked flask, and were stirred to dissolve. The temperature was controlled at 0~5° C. The above liquid A was slowly added dropwise at an appropriate speed so that the temperature of the reaction solution did not exceed 5° C. After dropping, the reaction was heated to 20-25° C. and reacted for 30 min, and then 500 ml of glacial acetic acid was added dropwise. After the addition, the mixture was concentrated under reduced pressure at 40-45° C. until it was drained. The residue was extracted 5 times with ethyl acetate, 2000 ml each time. The extract liquor was combined, and anhydrous sodium sulfate was added to dry and dewater for 2 h, and then filtered; the filtrate was collected and concentrated under reduced pressure at 40~45° C. until it was drained to obtain the product A7.

Weighing, purity detection and yield calculation were carried out using the same methods as those in Example 1.

The results showed that 69.2 g of the product was obtained in the hectogram-level preparation process, with a purity of 99.15% and a yield of 62.79%.

Kilogram-Level

At room temperature and under the protection of nitrogen gas (the reaction process is also under nitrogen gas), 1.6 Kg of A6 and 25 L of anhydrous tetrahydrofuran were added to a 50 L glass reactor (with heating and cooling liquid interlayer), and were stirred to dissolve. 2.0 Kg of N,N'-carbonyldiimidazole was added, and heated to 45~50° C. and reacted for 30 min, and then cooled to 20~25° C. and reacted for 30 min, and the sample as detected by HPLC contained less than 1.0% of the raw material A6. Liquid A was obtained and reserved.

At 0~5° C., 1515 g of sodium borohydride and 20 L of $H_2O$ were added to another 50 L glass reactor (with heating and cooling liquid interlayer), and were stirred to dissolve. The temperature was controlled at 0~5° C. The above liquid A was slowly added dropwise at an appropriate speed so that the temperature of the reaction solution did not exceed 5° C. After dropping, the reaction was heated to 20-25° C. and reacted for 30 min, and then 5 L of glacial acetic acid was added dropwise. After the addition, the mixture was concentrated under reduced pressure at 40~45° C. until it was drained. The residue was extracted 5 times with ethyl acetate, 10 L each time. The extract liquor was combined, and anhydrous sodium sulfate was added to dry and dewater for 2 h, and then filtered; the filtrate was collected and concentrated under reduced pressure at 40-45° C. until it was drained to obtain product A7.

Weighing and purity detection were carried out using the same methods as those in Example 1. The results showed that the above product A7 was 1.8 Kg yellow viscous solid.

Considering the low purity of the product, this example further carried out refining using the following methods:

The above crude product A7 was dispersed into 2.5 L ethanol at −10-0° C., stirred at low speed for 30-60 minutes, filtered, and the filter cake was washed with cold ethyl acetate to obtain the purified product.

The purified product was weighed, purity detected and yield calculated. The results showed that after refining and purifying, 880 g final product was obtained with the purity of 98.8%, and the yield of 60.0%.

The above content is a further detailed description of the present application in conjunction with the specific embodiments, and it cannot be deemed that the specific embodiments of the present application are limited to these descriptions. For the skilled person in the technical field to which the present application belongs, some simple deductions or substitutions can be made without departing from the concept of the present application.

What is claimed is:

1. A preparation process of 1-N-methyl-2-nitro-5-hydroxymethylimidazole, comprising reacting N,N'-carbonyldiimidazole and 1-N-methyl-2-nitro-5-carboxylic A acid imidazole at 45~65° C. for a period of time, and then cooled to 15~25° C. and reacted for a period of time until the reaction is complete, and then reacted with the reducing agent sodium borohydride or potassium borohydride to finally obtain 1-N-methyl-2-nitro-5-hydroxymethylimidazole.

2. The preparation process according to claim 1, comprising the following steps:

Step 1, N,N'-carbonyldiimidazole is added to a solution of 1-N-methyl-2-nitro-5-carboxylic acid imidazole, and the mixture is heated to 45~65° C. and reacts for a period of time, and then is cooled to 15~25° C. and reacts for a period of time until the reaction is complete to obtain liquid A;

Step 2, at 0~5° C., the aqueous solution of sodium borohydride or potassium borohydride is added dropwise to the liquid A at an appropriate speed so that the temperature of the reaction solution does not exceed 5° C.; after dropping, the reaction solution is heated to 15~25° C. until the reaction is complete; an acid is added to adjust the pH value to neutral or weakly acidic, and the organic solvent is removed by concentration under reduced pressure at 40~45° C.; the residue is extracted with an extractant, and the organic phase is collected; the organic phase is dewatered with a drying agent, and then filtered; the filtrate is collected, and concentrated under reduced pressure at 40~45° C. until it is drained to obtain the product 1-N-methyl-2-nitro-5-hydroxymethylimidazole.

3. The preparation process according to claim 2, characterized in that in step 1, a solvent in the solution of 1-N-methyl-2-nitro-5-carboxylic acid imidazole is tetrahydrofuran or dioxane, and 1 g of 1-N-methyl-2-nitro-5-carboxylic acid imidazole corresponds to 10-30 ml A of the solvent; and the feeding mass ratio of 1-N-methyl-2-nitro-5-carboxylic acid imidazole to N,N'-carbonyldiimidazole is 1:1.10-2.00.

4. The preparation process according to claim 2, characterized in that in step 1, the reaction time after heating to 45~65° C. is 20-40 minutes, and the reaction time after cooling to 15~25° C. is 20-40 minutes.

5. The preparation process according to claim 2, characterized in that in step 2, the mole ratio of the added sodium borohydride or potassium borohydride to 1-N-methyl-2-nitro-5-carboxylic acid imidazole is 3.0-4.0:1; and the concentration of sodium borohydride or potassium borohydride in the aqueous solution of sodium borohydride or potassium borohydride is 0.05-0.50 g/ml.

6. The preparation process according to claim 2, characterized in that in step 2, the acid for adjusting the pH value to neutral or weakly acidic is selected from at least one of formic acid, acetic acid and hydrochloric acid.

7. The preparation process according to claim 2, characterized in that in step 2, the extractant is selected from at least one of ethyl acetate, methyl acetate and dichloromethane; and the drying agent is selected from at least one of anhydrous sodium sulfate, anhydrous calcium sulfate, anhydrous calcium chloride and anhydrous magnesium sulfate.

8. The preparation process according to claim 2, characterized by further comprising step 3, refining and purifying the product 1-N-methyl-2-nitro-5-hydroxymethylimidazole obtained by concentration under reduced pressure at 40~45° C. until it is drained; wherein the refining and purifying include that the product concentrated under reduced pressure is dispersed into ethanol, and filtered; the filter cake is washed with ethyl acetate to obtain purified 1-N-methyl-2-nitro-5-hydroxymethylimidazole.

9. The preparation process according to claim 5, characterized in that in step 2, the mole ratio of the added sodium borohydride or potassium borohydride to 1-N-methyl-2-nitro-5-carboxylic acid imidazole is 3.5-4.0:1.

10. The preparation process according to claim 5, characterized in that in step 2, the concentration of sodium borohydride or potassium borohydride in the aqueous solution of sodium borohydride or potassium borohydride is 0.05-0.15 g/ml.

11. The preparation process according to claim 6, characterized in that the pH value is adjusted to 5-6.

* * * * *